(12) United States Patent
Wang

(10) Patent No.: US 11,400,060 B2
(45) Date of Patent: Aug. 2, 2022

(54) USE OF KETAMINE IN THE TREATMENT OF CACHEXIA

(71) Applicant: Astromedical Biotechnology, Ltd., New Taipei (TW)

(72) Inventor: James Chyan-Ji Wang, Newport Beach, CA (US)

(73) Assignee: ASTROMEDICAL BIOTECHNOLOGY, LTD., New Taipei (TW)

( * ) Notice: Subject to any disclaimer, the term of this patent is extended or adjusted under 35 U.S.C. 154(b) by 0 days.

(21) Appl. No.: 16/952,729

(22) Filed: Nov. 19, 2020

(65) Prior Publication Data

US 2021/0212965 A1    Jul. 15, 2021

Related U.S. Application Data

(60) Provisional application No. 62/960,255, filed on Jan. 13, 2020.

(51) Int. Cl.
*A61K 31/135*  (2006.01)
*A61P 21/06*   (2006.01)
*A61K 31/513*  (2006.01)

(52) U.S. Cl.
CPC .......... *A61K 31/135* (2013.01); *A61K 31/513* (2013.01); *A61P 21/06* (2018.01)

(58) Field of Classification Search
CPC ...... A61K 31/135; A61K 31/513; A61P 21/06
See application file for complete search history.

(56) References Cited

U.S. PATENT DOCUMENTS

| | | | |
|---|---|---|---|
| 6,365,607 | B1 | 4/2002 | Momose et al. |
| 8,309,570 | B2 | 11/2012 | Sang |
| 2010/0074955 | A1 | 3/2010 | Buschmann et al. |
| 2016/0228357 | A1 | 8/2016 | Lichter et al. |
| 2020/0002412 | A1 | 1/2020 | Hendifar |

FOREIGN PATENT DOCUMENTS

| | | |
|---|---|---|
| WO | WO 2006/091862 | 8/2006 |
| WO | WO 2019/169165 A1 | 9/2019 |

OTHER PUBLICATIONS

International Search Report for International Application No. PCT/US2020/061187, dated Feb. 9, 2021.

*Primary Examiner* — Savitha M Rao
(74) *Attorney, Agent, or Firm* — Birch, Stewart, Kolasch & Birch, LLP

(57) ABSTRACT

Disclosed herein is an use of ketamine in the treatment of cachexia, wherein the ketamine is administered to a subject who is treated with 5-FU and the dose amount of ketamine is about 60% to 5-FU. Specifically, the ketamine in the present invention is used to elevate the survival rate and improve the reduction of weight caused by cachexia.

6 Claims, No Drawings

USE OF KETAMINE IN THE TREATMENT OF CACHEXIA

CROSS REFERENCE

This Non-provisional application claims the priority under 35 U.S.C. § 119(e) on U.S. Patent Provisional Application No. 62/960,255 filed on Jan. 13, 2020, the entire contents of which are hereby incorporated by reference.

FIELD OF THE INVENTION

The present invention relates to a use of ketamine in the treatment of cachexia; and, in particular, ketamine is used for treating cachexia caused by 5-FU treatment.

BACKGROUND OF THE INVENTION

5-Fluorouracil (5-FU) has been used in cancer treatment for nearly 50 years and can be used to treat a variety of cancers. Although it is effective in treating cancer, it also produces a large number of side effects, such as nausea, vomiting, diarrhea, mucosal inflammation, headache, muscle weakness, hair loss, myocardial infarction, or pneumonia. Therefore, taking 5-FU is a great burden for cancer patients.

Cachexia (also known as cachexy) is a complex metabolic syndrome caused by the disease. Poor metabolism and anorexia nervosa in the syndrome often cause abnormal weakness in patients, and the main symptom includes muscle loss and weight loss. Other symptoms include decreased albumin and hemoglobin, and increased inflammatory factors (e.g., interleukin-6 (IL-6) and reactive protein (CRP)). The muscle wasting symptoms of cachexia cannot be recovered by simply supplying nutrients. Even if food intake is increased or nutritional intake is increased, the continuous weight loss in patients cannot be prevented or stopped.

The current treatment methods can only relieve symptoms by treating diseases that cause cachexia (such as cancer), but they are often ineffective and difficult to heal. Usually, the deterioration of cachexia is alleviated through muscle activity, administration of drugs that stimulate appetite or reduce nausea, direct administration of nutritional drugs, or other supportive therapies. Therefore, there is an urgent need to develop a drug or method that can effectively improve the syndrome of cachexia, so that the survival rate of cancer patients can be improved.

SUMMARY OF THE INVENTION

An aspect provided herein is a method for the treatment of cachexia, comprising administering to a subject treated with 5-FU a therapeutically effective amount of ketamine.

In a particular embodiment, wherein a human dose of the ketamine is 1-100 mg/60 kg per week.

In a particular embodiment, wherein the ketamine is administered parenterally.

In a particular embodiment, wherein the treatment improves the loss of weight due to cachexia.

In a particular embodiment, wherein the treatment increases survival rate.

Another aspect provided herein is a pharmaceutical composition for the treatment of cancer, including: 5-FU, ketamine, and a pharmaceutically acceptable carrier; wherein a human dose of the ketamine is 1-100 mg/60 kg per week.

Another aspect provided herein is a method for the treatment of cancer, comprising administering to a subject in need a therapeutically effective amount of a pharmaceutical composition comprising 5-FU and ketamine.

In a particular embodiment, wherein a human dose of the ketamine is 1-100 mg/60 kg per week.

In a particular embodiment, wherein the pharmaceutical composition is administered parenterally.

In a particular embodiment, wherein the ketamine and the 5-FU are administered concurrently or separately.

DESCRIPTION OF THE INVENTION

The following embodiments when read are made to clearly exhibit the above-mentioned and other technical contents, features and effects of the present disclosure. Through the description by means of the embodiments, a person of ordinary skills in the art would explicitly understand the technical approach and effects the present disclosure adopts to achieve the above-identified aspect.

Unless otherwise defined, all the technical and scientific terms used herein have the same definition as commonly understood by a person of ordinary skills in the art to which the present disclosure pertains.

As used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and is not "included," limiting. The section headings used herein are for organizational purposes only and are not to be construed as limiting the subject matter described. Unless otherwise specified, all the material used herein is commercial and can be easily obtained.

The term "about" used herein refers to a measured quantity, such as dose, including the deviation±15% or ±10% relative to a specified quantity in an embodiment; the deviation±5% relative to a specified quantity in a preferred embodiment; the deviation±1% relative to a specified quantity in a further preferred embodiment; or the deviation±0.1% relative to a specified quantity in a most preferred embodiment; whereas the nature of the substance the quantity pertains to is not affected thereby.

5-Fluorouracil (briefly referred to as 5-FU in this specification) is a kind of pyrimidine analogs, and is mainly used for the treatment of tumors. It is currently believed that the mode of action of 5-FU is to further hinder DNA synthesis by inhibiting the function of thymidylate synthase.

The side effects of 5-FU include severe dehydration, bone marrow suppression, enteritis, oral ulcers, dermatitis, angina and myocardial infarction, acute renal insufficiency, interstitial pneumonia, liver damage, jaundice, diarrhea, and so on. 5-FU can also cause acute central nervous system damage (leukoencephalopathy) and central nervous system degeneration.

Ketamine (IUPAC: (R,S)-2-(2-chlorophenyl)-2-methyl-amino-cyclohexan-1-one), also known as special K, is a non-competitive NMDA receptor antagonist, and has been widely used for anesthesia, analgesia, and sedation since the 1960s. Ketamine is metabolized by liver cytochrome P450 and binds to various receptors including NMDA to create anesthetic effect.

Ketamine can inhibit the activation of NMDA receptors induced by glutamine (a neurotransmitter of the central nervous system), and can also inhibit the release of glutamine from presynaptic neurons and enhance the effect of the inhibitory neurotransmitter GABA.

In this specification, "ketamine" may refer to the form of racemic or enantiomerically enriched (for example, enantiomerically pure). In one embodiment, the ketamine described in the present invention is racemic ketamine. In another embodiment, the ketamine described in the present invention is enantiomerically enriched ketamine. In a specific embodiment, the ketamine described in the present invention is an S-mirror isomer or an R-mirror isomer.

In this specification, the dose of a drug is defined as the weight of the drug administered per kilogram of body weight, for example: the grams of drug administered per kilogram of body weight (g/kg) or the number of milligrams of drug administered per kilogram of body weight (mg/kg).

The terms "about" or "approximately" used in this specification refer to the acceptable degree of deviation understood by those skilled in the art, which may vary to a certain extent according to the usage in the text. Generally speaking, for example, "about" or "approximately" may refer to values in the range of ±10%, ±5%, or ±3% thereof.

The terms "treatment", "improvement" or similar terms thereof in this specification include alleviating, mitigating, or improving at least one disease symptom or physical condition by means of treatment or prevention, preventing new symptoms, inhibiting disease or physiological conditions, preventing or slowing down the development of diseases, causing the recovery of diseases or physiological conditions, slowing down the physiological conditions caused by diseases, and stopping disease symptoms or physiological conditions.

The term "cachexia" (also known as cachexy) in this specification refers to symptoms caused by persistent severe weight loss, anorexia, weakness, anemia, and abnormal metabolism of protein, fat, and carbohydrate. Cachexia is clinically defined as a syndrome with anorexia, anemia, and weight loss as the main symptoms. Cachexia can occur in a variety of conditions, including tumors, chemotherapy, anorexia, severe trauma, gastrointestinal malabsorption, weight loss, anemia, obesity, and severe sepsis, among which tumor-induced cachexia is the most common and is called tumor cachexia.

The pharmaceutical composition of the present invention can be used to treat cachexia in a subject. Specifically, the pharmaceutical composition of the present invention can be administered to a subject who is at risk of developing cachexia or experiencing symptoms related to cachexia, so as to avoid the occurrence of cachexia or to improve or delay the progression of cachexia.

The term "effective amount" or "therapeutically effective amount" in this specification refers to a sufficient amount of a compound or drug that can alleviate one or more disease symptoms or physiological conditions after the patient takes the drug. The result is to reduce and/or alleviate signs, symptoms, or causes, or intentional changes in other physiological systems. For example, the "effective amount" for treatment includes a dose of the compound provided by the present invention that can significantly reduce the symptoms of the disease in clinical practice.

According to the present invention, the therapeutically effective amount varies depending on the severity of the disease, the age of the patient, the health status of the patient, the potential risk of cancer, or other factors.

According to the present invention, the composition described in this specification and other pharmaceutical ingredients need not be administered in the same pharmaceutical composition, and may be administered in different ways due to different physical and chemical properties.

The term "composition" or "pharmaceutical composition" in this specification refers to a mixture of at least one drug and other carriers. The carriers include, but are not limited to, stabilizers, diluents, dispersants, suspending agents, thickening agents, excipients, or a combination thereof.

The term "pharmaceutically acceptable" in this specification refers to a compound, composition, and/or dosage form within the scope of reasonable medical judgment, suitable for use in contact with the tissues of the user (such as human), without excessive toxicity, irritation, allergic reaction, or other problems or complications, and with a quite reasonable benefit/risk ratio. Each carrier is "acceptable", provided that it must be compatible with other formulation ingredients.

The term "carrier" in this specification refers to a nontoxic compound or drug that has the function of assisting cells or tissues to absorb drugs.

Examples of suitable excipients include, but are not limited to: lactose, dextrose, sucrose, sorbose, mannose, starch, acacia, calcium phosphate, alginate, tragacanth, gelatin, calcium silicate, microcrystalline cellulose, polyvinylpyrrolidone, cellulose, sterilized water, syrup and methyl cellulose.

The composition may additionally include lubricants, for example, talc, magnesium stearate, and mineral oil; wetting agents; emulsifying and suspending agents; preservatives, for example, methyl and propyl hydroxybenzoate; sweetening agents; and flavoring agents.

According to the present invention, the drug of the present invention may be applied to a variety of administration techniques, including but not limited to intravenous injection, oral administration, parenteral administration, ocular administration, pulmonary administration, or local administration, or a combination of the above routes of administration.

According to the present invention, the drug of the present invention is used for intraperitoneal injection.

According to the present invention, the pharmaceutical composition can be in the form of troches, pills, powders, lozenges, sachets, tablets, elixirs, suspensions, emulsions, solvents, syrups, soft and hard gelatin capsules, suppositories, sterilized injection and packaged powder.

The present invention provides a method for treating cachexia caused by 5-FU, comprising: administering to a patient a therapeutically effective amount of ketamine, wherein the patient is receiving 5-FU treatment.

The present invention also provides a use of ketamine for preparing a medicine for improving cachexia, wherein the medicine is administered to a patient receiving 5-FU treatment.

In a preferred embodiment, the drug is used to improve weight loss caused by cachexia.

In a preferred embodiment, the drug is used to improve survival rate.

The present invention also provides a method for treating cancer, comprising: administering a therapeutically effective amount of a pharmaceutical composition to a patient, wherein the pharmaceutical composition includes: 5-FU, ketamine, and a pharmaceutically acceptable carrier.

In a preferred embodiment, the cancer includes, but is not limited to: anal cancer, breast cancer, colorectal cancer, oropharyngeal cancer, gastric cancer, pancreatic cancer, skin cancer, or head and neck cancer.

In a preferred embodiment, the ketamine and the 5-FU are administered to the patient simultaneously or separately.

The present invention also provides a pharmaceutical composition for treating cancer, comprising: 5-FU, ketamine, and a pharmaceutically acceptable carrier.

In a preferred embodiment, the dose of ketamine in the pharmaceutical composition is at least about 60% of the dose of 5-FU.

In a preferred embodiment, a human dose of the ketamine is 1-100 mg/60 kg per week.

In a more preferred embodiment, a human dose of the ketamine is 1-50 mg/60 kg per week.

In a preferred embodiment, a human dose of the ketamine is about 25 mg/60 kg per week.

The anti-tumor drug, capecitabine, is absorbed orally and converted into 5-FU in the tissues to exert an anti-tumor effect. Therefore, in a particular embodiment, the 5-FU can be administered to the patient in the form of capecitabine.

Norketamine (IUPAC: (R,S)-2-(2-chlorophenyl)-2-(amine)cyclohexanone) is the metabolite of ketamine after demethylation, and has lower and slower activity than ketamine.

Therefore, in a specific embodiment, the ketamine can be administered to the patient in the form of norketamine. In this specification, "norketamine" may refer to the form of racemic or specular isomer enrichment (for example, pure specular isomerism).

Examples

Materials and Methods 6 to 12-week-old mice (taken from the National Laboratory Animal Center) were individually raised in a temperature-controlled room under a 12-hour light/12-hour dark cycle and a temperature of 24±1° C.

The mice were divided into 4 groups, with 4 mice in each group.

5-FU was formulated as a dose of 50 mg per kilogram (50 mg/kg) in mice, and injected intraperitoneally (i.p.) once a day for 3 consecutive days.

In addition, Ketamine was prepared at a dose of 15 mg/kg or 30 mg/kg, and injected into the abdominal cavity of mice (i.p.) 24 hours after the last injection of 5-FU.

Saline was used as the carrier of 5-FU and ketamine as well as the control group.

After the above injection was completed, the survival rate, body weight, and food intake of the mice were observed.

Experimental Results

The experimental results of this example are disclosed in Tables 1 to 3.

It can be known from the results that mice in all groups received 50 mg/kg 5-FU intraperitoneal injection, but on the 17th day after 5-FU injection, the group injected with 50 mg/kg 5-FU and 15 mg/kg ketamine had a survival rate of 25% only. However, there is still a 100% survival rate in the groups of 50 mg/kg 5-FU and 30 mg/kg ketamine.

Secondly, regarding the food intake, the control group consumed 235.2 grams (g) of food (standard deviation: 4.0). The 5-FU injection group received 189.6 g of food (standard deviation: 7.5). The two groups given 5-FU and ketamine respectively have similar intake. The group of 15 mg/kg ketamine took 215.0 g of food (standard deviation: 8.3); and the group of 30 mg/kg of ketamine took 219.1 g of food (standard deviation: 5.7).

Furthermore, regarding weight changes, mice in the group injected with 50 mg/kg of 5-FU and 15 mg/kg of ketamine lost an average of 19.9% in body weight, similar to the group injected with 5-FU only. In contrast, in the group of 50 mg/kg 5-FU and 30 mg/kg ketamine, the weight loss was only 7.5%, which was closer to that of the control group (0.2% reduction).

TABLE 1

Weight of mice in Last Observation Carried Forward (LOCF) population at the end of experiments

| Treatment | Weight (g) Average (s.d.)/ Median | Food intake (g) Average (s.d.) | Water consumption (ml) Average (s.d.) | Survival rate (%) |
|---|---|---|---|---|
| Control group | 21.1 (0.7) 21.0 | 235.2 (4.0) | 200.19 (3.0) | 100 |
| 5-FU (50 mg/kg) | 17.6 (2.7) 16.4 | 189.6 (7.5) | 149.6 (3.3) | 25 |
| 5-FU (50 mg/kg) + ketamine (15 mg/kg) | 17.6 (4.0) 17.1 | 215.1 (8.3) | 140.3 (3.9) | 25 |
| 5-FU (50 mg/kg) + ketamine (30 mg/kg) | 20.5 (2.9) 21.2 | 219.0 (5.7) | 188.8 (3.0) | 100 | s.d.: Standard deviation

TABLE 2

Changes in body weight of mice in LOCF population at the end of the experiment

| Treatment | Average of body weight change (g) from baseline (s.d.)/Median | Average of Food intake (g) (s.d.) | Survival rate (%) |
|---|---|---|---|
| Control group | −0.0 (0.5)/ 0.1 | 235.2 (4.0) | 100 |
| 5-FU (50 mg/kg) | −4.4 (3.1)/ −5.7 | 189.6 (7.5) | 25 |
| 5-FU (50 mg/kg) + ketamine (15 mg/kg) | −4.3 (3.6)/ −4.6 | 215.1 (8.3) | 25 |
| 5-FU (50 mg/kg) + ketamine (30 mg/kg) | −1.6 (2.4)/ −1.1 | 219.0 (5.7) | 100 |

TABLE 3

Percentage of change in body weight of mice in LOCF population at the end of the experiment

| Treatment | Average of body weight change percentage from baseline (s.d.)/Median | Average of Food intake (g) (s.d.) | Survival rate (%) |
|---|---|---|---|
| Control group | −0.2 (2.5)/ 0.5 | 235.2 (4.0) | 100 |
| 5-FU (50 mg/kg) | −19.9 (13.8)/ −25.6 | 189.6 (7.5) | 25 |
| 5-FU (50 mg/kg) + ketamine (15 mg/kg) | −19.9 (16.5)/ −21.3 | 215.1 (8.3) | 25 |
| 5-FU (50 mg/kg) + ketamine (30 mg/kg) | −7.5 (11.1)/ −4.9 | 219.0 (5.7) | 100 |

According to the content disclosed in this application, it can be learned from animal experiments that 5-FU injection may cause symptoms and complications of cachexia such as weight loss, reduced food and water intake and reduced survival rate, and co-administration of ketamine can improve the above symptoms. Therefore, people having ordinary skills in the art can learn from this specification that ketamine can be used to improve or treat cachexia caused by 5-FU.

While preferred embodiments of the present disclosure have been shown and described herein, it will be obvious to those skilled in the art that such embodiments are provided by way of example only and can be implemented in combinations. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

I claim:

1. A method for the treatment of cachexia induced by a chemotherapy drug for treating a cancer, comprising administering to a subject in need thereof a therapeutically effective amount of ketamine.

2. The method of claim 1, wherein a human dose of the ketamine is 1-100 mg/60 kg per week.

3. The method of claim 1, wherein the ketamine is administered parenterally.

4. The method of claim 1, wherein the ketamine improves the loss of weight due to cachexia in the subject.

5. The method of claim 1, wherein the ketamine increases survival rate of the subject.

6. The method of claim 1, wherein the chemotherapy drug is Fluorouracil (5-FU).

\* \* \* \* \*